(12) United States Patent
DeJong

(10) Patent No.: US 10,618,072 B2
(45) Date of Patent: Apr. 14, 2020

(54) INLINE VACUUM SPRING SUSTAINED DURATION SPRAYER

(71) Applicant: Silgan Dispensing Systems Corporation, Grandview, MO (US)

(72) Inventor: David L. DeJong, Ogden, UT (US)

(73) Assignee: Silgan Dispensing Systems Corporation, Grandview, MO (US)

(*) Notice: Subject to any disclaimer, the term of this patent is extended or adjusted under 35 U.S.C. 154(b) by 0 days.

(21) Appl. No.: 16/327,477

(22) PCT Filed: Aug. 22, 2017

(86) PCT No.: PCT/US2017/047932
§ 371 (c)(1),
(2) Date: Feb. 22, 2019

(87) PCT Pub. No.: WO2018/044617
PCT Pub. Date: Mar. 8, 2018

(65) Prior Publication Data
US 2019/0176178 A1 Jun. 13, 2019

Related U.S. Application Data

(60) Provisional application No. 62/380,569, filed on Aug. 29, 2016.

(51) Int. Cl.
*B05B 11/00* (2006.01)
*B05B 9/00* (2006.01)
*A61B 5/00* (2006.01)
*B05B 9/08* (2006.01)

(52) U.S. Cl.
CPC ............ *B05B 11/3011* (2013.01); *A61B 5/00* (2013.01); *B05B 9/00* (2013.01); *B05B 11/3002* (2013.01); *B05B 11/3014* (2013.01); *B05B 9/085* (2013.01); *B05B 11/3057* (2013.01)

(58) Field of Classification Search
CPC .............. B05B 11/085; B05B 11/3002; B05B 11/3011; B05B 11/3014; B05B 11/3057
USPC ............. 222/189.1, 190, 321.7, 321.9, 383.1
See application file for complete search history.

(56) References Cited

U.S. PATENT DOCUMENTS

| 3,777,945 | A | * | 12/1973 | Nozawa | B05B 9/0883 222/394 |
|---|---|---|---|---|---|
| 3,797,748 | A | * | 3/1974 | Nozawa | B05B 9/0883 239/321 |
| 4,196,828 | A | * | 4/1980 | Basile | B05B 9/0883 222/340 |
| 5,641,097 | A | * | 6/1997 | Renault | B05B 11/3011 222/321.2 |
| 6,206,303 | B1 | * | 3/2001 | Shinozaki | B05B 11/0064 222/321.2 |
| 6,386,399 | B1 | * | 5/2002 | Tsujii | B05B 11/0059 222/376 |
| 6,644,516 | B1 | * | 11/2003 | Foster | B05B 7/0031 222/190 |

(Continued)

*Primary Examiner* — Vishal Pancholi
(74) *Attorney, Agent, or Firm* — Barlow Josephs and Holmes Ltd; Stephen Holmes

(57) ABSTRACT

A sustained duration trigger sprayer includes a first vacuum formed by piston movement in a fluid cylinder which fills the sprayer for delivery of a fluid and a second vacuum formed between a vacuum piston connected to the fluid cylinder and a vacuum cylinder acts on the sprayer to disperse product when a discharge valve is opened.

17 Claims, 12 Drawing Sheets

(56) References Cited

U.S. PATENT DOCUMENTS

| | | | | |
|---|---|---|---|---|
| 6,840,408 B1* | 1/2005 | Foster | ................ | B05B 11/3074 |
| | | | | 222/190 |
| 7,717,301 B2* | 5/2010 | Tsai | .................... | B05B 11/3087 |
| | | | | 222/190 |
| 2005/0276707 A1* | 12/2005 | Ophardt | ............... | A47K 5/1207 |
| | | | | 417/437 |
| 2010/0135834 A1* | 6/2010 | Tseng | ................ | B05B 11/3001 |
| | | | | 417/521 |

* cited by examiner

INLINE VACUUM SPRING SUSTAINED DURATION SPRAYER

BACKGROUND OF THE INVENTION

Field of the Invention

Embodiments of the invention relate generally to dispensing devices and more particularly to sustained duration sprayers.

State of the Art

Spray devices, such as trigger sprayers and other fine mist pumps, are well known and commonly used to disperse a product from a container or other source of product. Such devices typically deliver or spray a fixed amount of product with each actuation of a trigger or actuator associated with the device. Unlike aerosol-type sprayers, a user must continually actuate the device in order to receive a continuous spray or semi-continuous spray. While such systems are generally acceptable for most uses, there is a desire to have devices that allow for longer duration sprays or continuous sprays that are closer to the type of spray found with aerosol sprayers. Such sprayers are often referred to as sustained duration sprayers.

While many different types of sustained duration sprayers exist in the commercial markets, they are typically larger and bulkier than trigger sprayers and fine mist sprayers. In addition, such sustained duration sprayers are often made up of more parts than conventional sprayers, resulting in increased production costs and less aesthetically pleasing solutions. Therefore, improvements in existing sustained duration spray technology are desired. In addition, new systems for creating and delivering a sustained duration spray are desirable.

BRIEF SUMMARY OF THE INVENTION

Various embodiments of the invention relate to a sprayer, and more particularly a trigger sprayer, capable of providing a sustained duration spray. A sprayer according to various embodiments of the invention may include two vacuum systems: a first vacuum to fill a fluid chamber for distribution of the fluid and a second vacuum to facilitate movement of components of the sprayer to distribute the fluid from the fluid chamber.

According to some embodiments of the invention, a sprayer may include a head and a base, the base including a vacuum cylinder chamber configured to interact with a vacuum piston fitted to a portion of the head. A fluid cylinder chamber may be configured to interact with a piston wherein movement of the piston in the fluid cylinder chamber produces a vacuum capable of drawing a fluid or product into the fluid cylinder chamber. A valve associated with, or in fluid communication with, the fluid cylinder chamber, may be opened to allow fluid to escape the fluid cylinder chamber. When the valve is opened, fluid may be pushed from the fluid cylinder chamber as a result of movement caused by the vacuum in the vacuum cylinder.

According to various embodiments of the invention, a sustained duration sprayer may include a head, a base fitted to the head, and a fluid cylinder connected to the base. The head may include an outer shroud, a piston rod having a fluid discharge passage therein, a secondary discharge passage and a valve seat between the fluid discharge passage and the secondary discharge passage. The head may also include a vent post or occlusion member configured to open and close a vent in the base as the head is moved relative to the base.

A discharge valve may be seated in the valve seat and configured to open upon actuation of a trigger or button in communication therewith. Upon opening, fluid may flow through the fluid discharge passage and into the secondary discharge passage.

The base may include a connection for fitting the base—and the sprayer—to a container or bottle. The base may also include a vacuum cylinder chamber. An opening or conduit in the base may provide a vent path from atmosphere to a container or bottle connected to the base when a vent post or occlusion member is moved or unseated from the opening.

A fluid cylinder may be seated in the base or connected thereto. The piston rod of the head may be connected to a piston which is seated on an interior portion of the fluid cylinder. A static seal may seal off a portion of the fluid cylinder and the piston rod may pass through the static seal. The joinder between the piston rod and the static seal may be fluid tight such that product in the fluid cylinder will not leak through the connection between the piston rod and static seal.

As the head is moved relative to the base, the piston rod may push the piston into the fluid cylinder, creating a vacuum therein between the static seal and the piston. The creation of the vacuum may draw fluid into the fluid cylinder. For example, the fluid cylinder may include an inlet sealed by a portion of the static seal. As a vacuum is formed in the fluid cylinder, fluid or product may be drawn through the inlet into the fluid cylinder.

As fluid is drawn into the fluid cylinder, a vacuum piston attached to the first end of the fluid cylinder moves in the vacuum cylinder, creating a vacuum therein. Once created, the vacuum force is sufficient to move the head when the valve is opened. Thus, as a user actuates the sprayer, the valve is opened allowing fluid to flow from the fluid cylinder and allowing the vacuum force in the vacuum cylinder to act on the head, moving it upwards and pushing fluid out of the fluid cylinder.

BRIEF DESCRIPTION OF THE DRAWINGS

While the specification concludes with claims particularly pointing out and distinctly claiming particular embodiments of the present invention, various embodiments of the invention can be more readily understood and appreciated by one of ordinary skill in the art from the following descriptions of various embodiments of the invention when read in conjunction with the accompanying drawings in which:

DETAILED DESCRIPTION OF THE INVENTION

Detailed descriptions of various embodiments of the invention are described herein. It will be understood that the disclosed embodiments are merely examples of the way in which certain aspects of the invention can be implemented and do not represent an exhaustive list of all of the ways the invention may be embodied. As used herein, the word "exemplary" is used expansively to refer to embodiments that serve as illustrations, specimens, models, or patterns. Indeed, it will be understood that the trigger sprayers and devices described herein may be embodied in various and alternative forms. The Figures are not necessarily to scale and some features may be exaggerated or minimized to show details of particular components. Well-known components, materials or methods are not necessarily described in great detail in order to avoid obscuring the present disclosure. Any specific structural and functional details disclosed herein are not to be interpreted as limiting, but merely as a basis for the claims and as a representative basis for teaching one skilled in the art to variously employ the invention.

Figure 1:
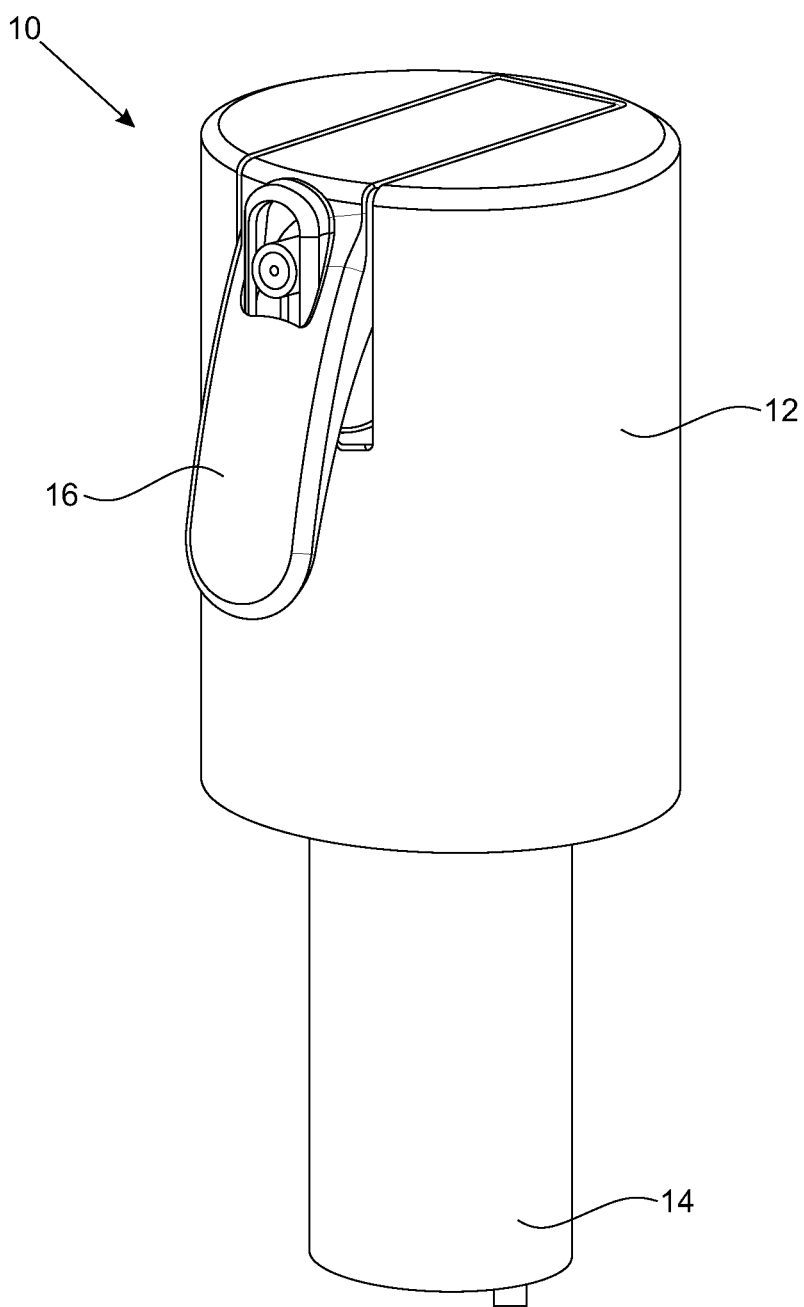
FIG. 1 is a perspective view of a trigger sprayer.
Figure 2:
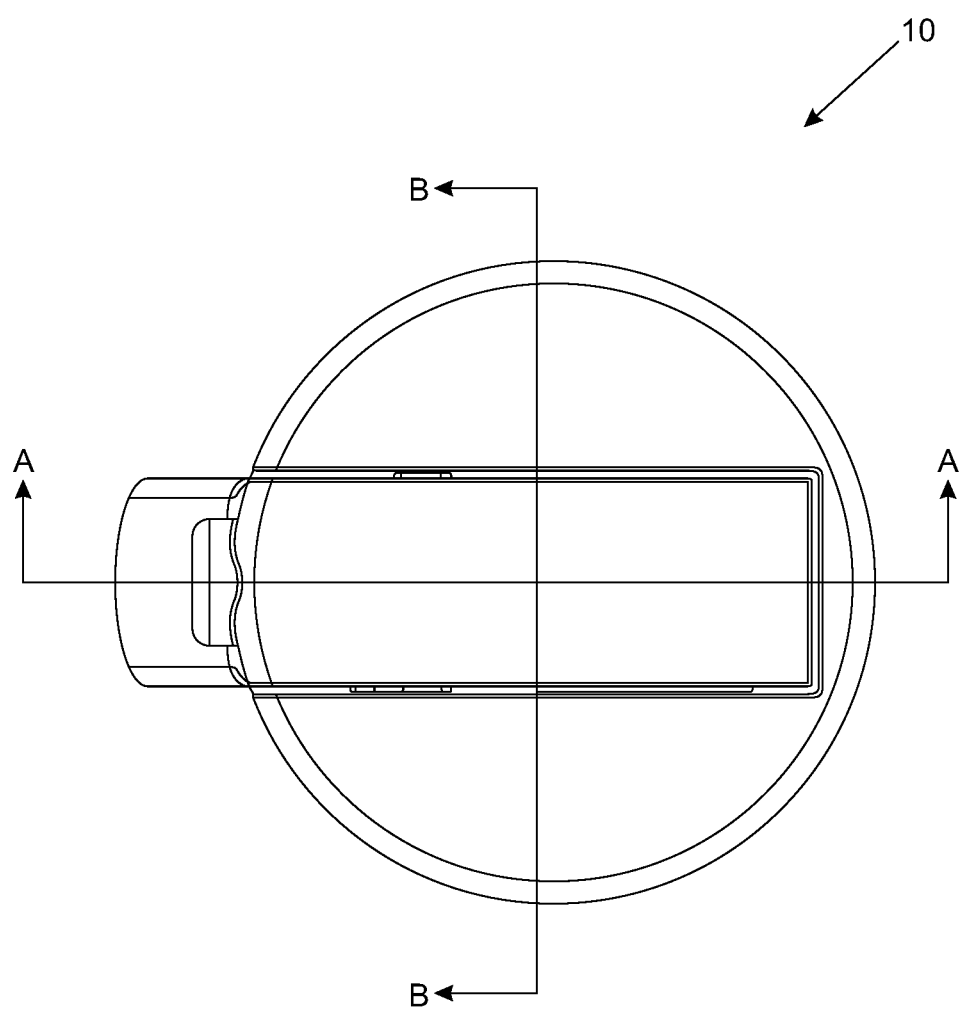
FIG. 2 is a top view of the trigger sprayer of FIG. 1.
Figure 2A:
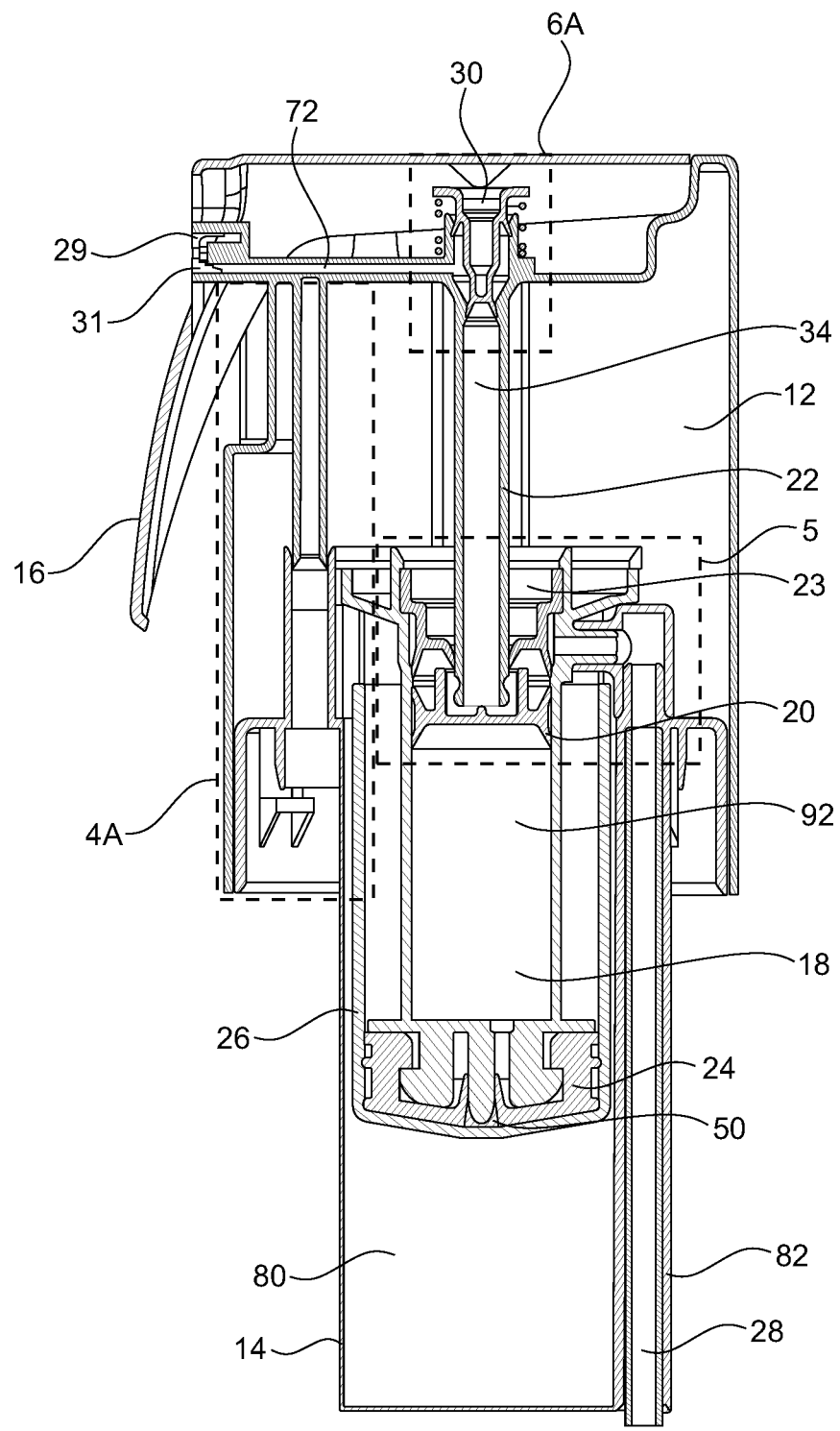
FIG. 2A is a cross-sectional view taken along the lines A-A of FIG. 2 when the trigger sprayer is in the non-actuated position.
Figure 2B:
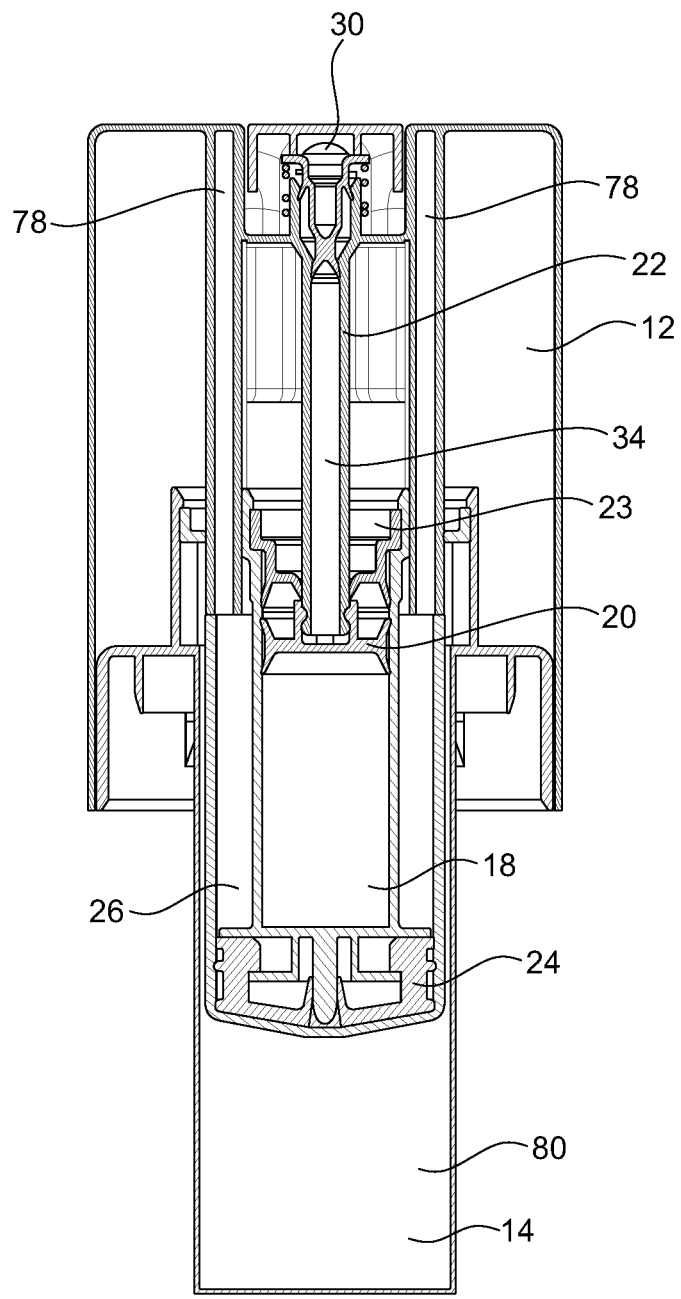
FIG. 2B is a cross-sectional view taken along the lines B-B of FIG. 2 when the trigger sprayer is in the non-actuated position.
Figure 3A:
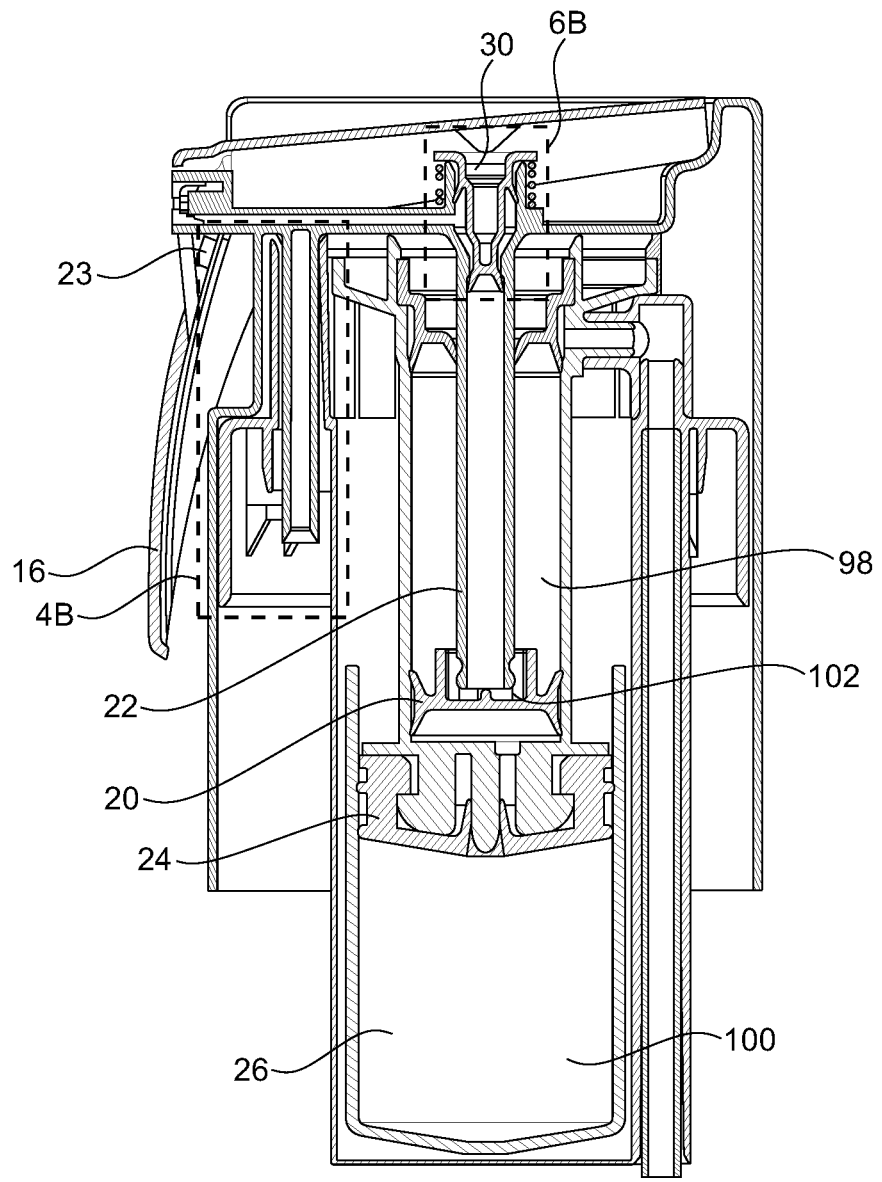
FIG. 3A is a cross-sectional view taken along the lines A-A of FIG. 2 when the trigger sprayer is in the actuated position.
Figure 3B:
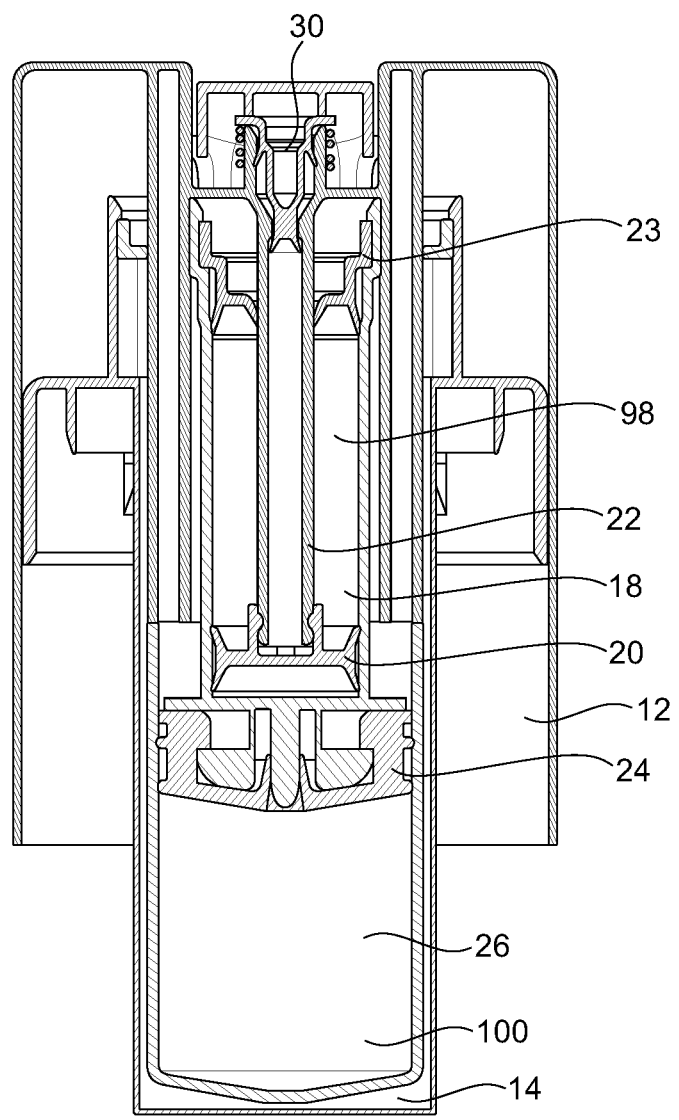
FIG. 3B is a cross-sectional view taken along the lines B-B when the trigger sprayer is in the actuated position.

Referring to FIGS. 1 and 2, a trigger sprayer 10 according to various embodiments of the invention is shown. FIGS. 2A and 2B show cross-sectional views of trigger sprayer 10 taken parallel to trigger 16 (FIG. 2A) and perpendicular to trigger 16 (FIG. 2B) as represented by lines A-A and B-B in FIG. 2. Trigger sprayer 10 may include a head 12 and base 14. Base 14 may be partially disposed within head 12. Trigger sprayer 10 is shown in FIGS. 1 and 2A-2B in a shipping or non-actuated position. Pressing down on head 12 causes base 14 to slide at least partially into the interior of head 12, thereby transitioning trigger sprayer 10 into an actuated position as shown in FIGS. 3A-3B.

Figure 7:
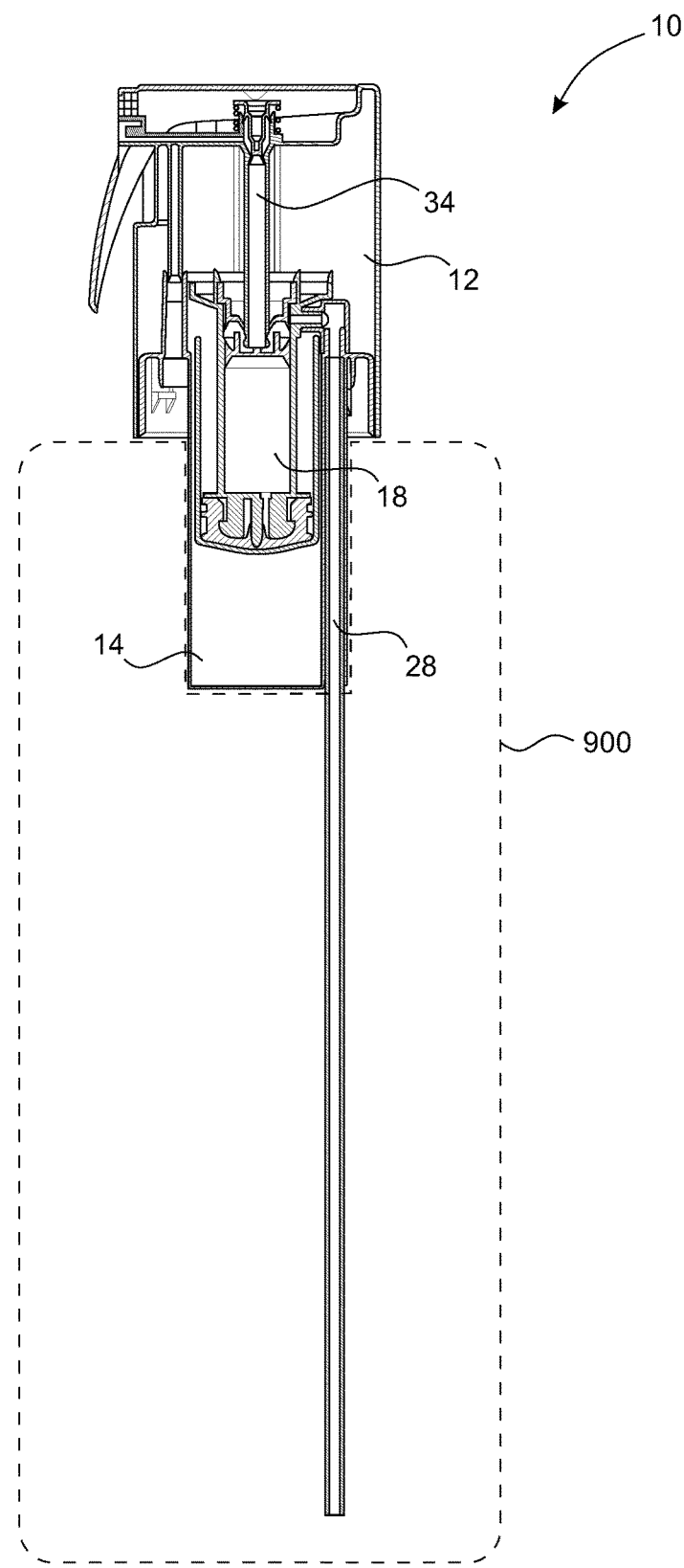
FIG. 7 illustrates a trigger sprayer according to various embodiments of the invention attached to a container.

A trigger sprayer 10 according to various embodiments of the invention may include a fluid cylinder 18 fixedly mounted within base 14. A piston 20 may be fixedly mounted to a hollow piston rod 22 at a lower end thereof. Piston rod 22 is in turn fixedly mounted within head 12 or is an integral part thereof. Piston rod 22 and piston 20 extend into the interior of fluid cylinder 18. A static seal 23 is fixedly mounted within fluid cylinder 18 at an upper end thereof, and about the exterior of piston rod 22. A vacuum piston 24 is fixedly mounted to fluid cylinder 18 at a lower end thereof. Fluid cylinder 18 and vacuum piston 24 are disposed within a vacuum cylinder 26. Vacuum cylinder 26 is disposed within base 14 but is fixedly mounted with respect to head 12 such that movement of head 12 moves the vacuum cylinder 26. Base 14 may include a dip tube 28 fluidly connected to a liquid/product source or container 900 as illustrated in FIG. 7. Vacuum piston 24 may include an integrated valve 50 that vents air out of the vacuum cylinder 26 during assembly of trigger sprayer 10.

Trigger sprayer 10 may also include a spring-biased discharge valve 30 that is at least partially disposed within an upper end of piston rod 22. The hollow interior of piston rod 22 defines part of a fluid discharge passage 34. Spring 36 ordinarily biases discharge valve 30 into a first or home position as illustrated in FIG. 6A in which an enlarged lower portion 40 of the discharge valve 30 is disposed snugly within a reduced-diameter portion 42 of fluid discharge passage 34 so as to close the fluid path through discharge passage 34.

Trigger sprayer 10 may be shipped in the non-actuated or shipping position shown in FIGS. 2A-2B. In this configuration, there is no fluid in the fluid cylinder 18. Pressing down on head 12 to move the sprayer into the actuated position moves the piston 20 down through fluid cylinder 18, creating a vacuum therein which causes a chevron or valve seal 94 integrated with the static seal 23 to deform open or unseat from an interior wall of the fluid cylinder 18. The vacuum also pulls liquid or product from a container or another source into an interior portion of the fluid cylinder 18. For example, as illustrated in FIG. 3A, when the piston 20 is pushed into the fluid cylinder 18, liquid or other product may be pulled by vacuum through the dip tube 28, through elbow 46, through inlet port 48 of fluid cylinder 18, past the valve seal 94 and into an interior of the fluid cylinder 18 between the piston 20 and the static seal 23.

Pressing down on the head 12 to move the trigger sprayer 10 into the actuated position also moves the vacuum cylinder 26 downward relative to vacuum piston 24, thereby creating a vacuum in an interior space of the vacuum cylinder 26. Trigger sprayer 10 is configured to stay in the actuated position until the trigger 16 is depressed to dispense the fluid/product contents from fluid cylinder 18. This is because the vacuum pressure in vacuum cylinder 26 which is attempting to urge head 12 up relative to base 14, is more than offset by the fluid pressure created within fluid cylinder 18.

Figure 6A:
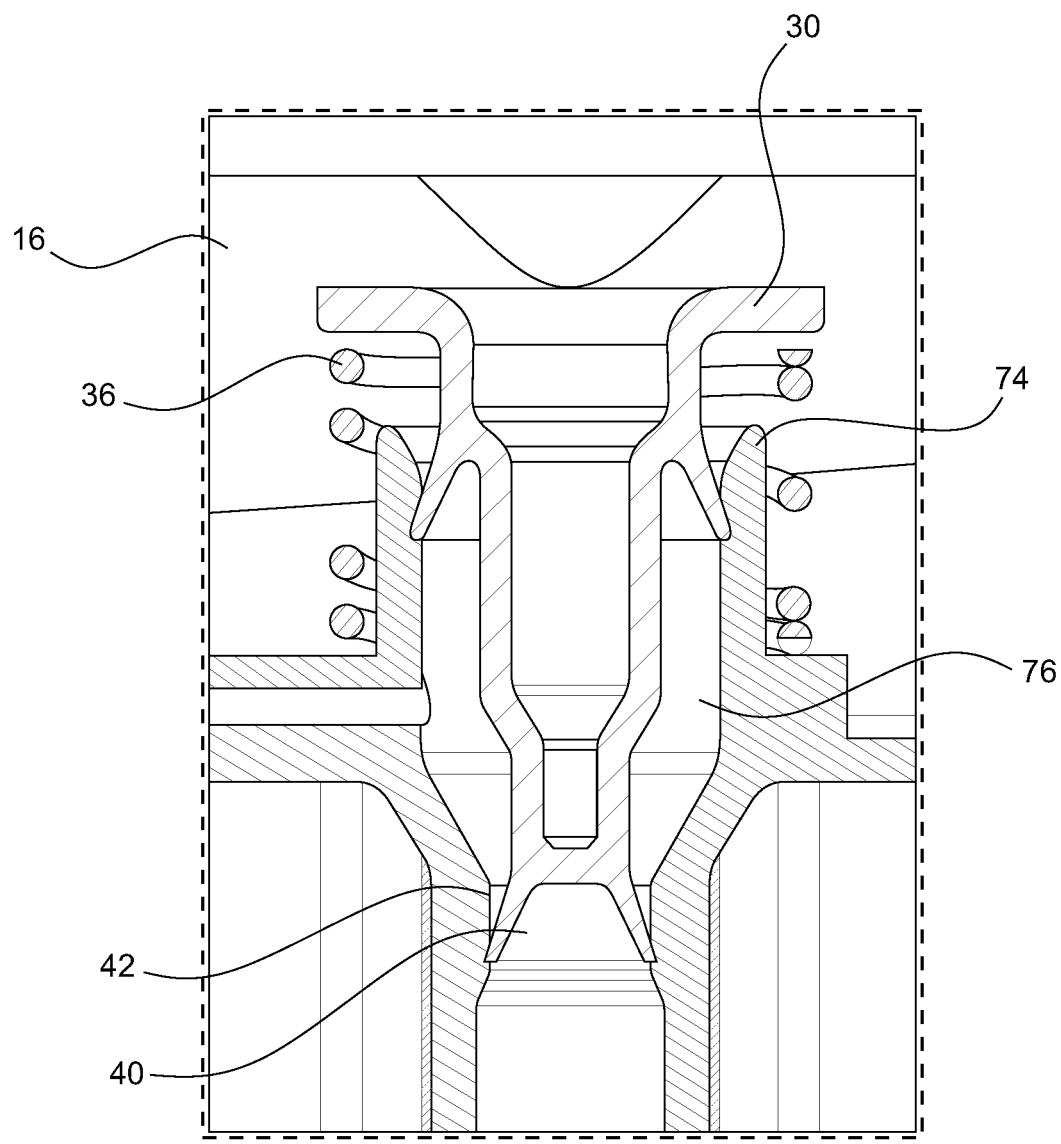
FIG. 6A is an enlarged view of the portion within the broken-line box labeled 6A in FIG. 2A.
Figure 6B:
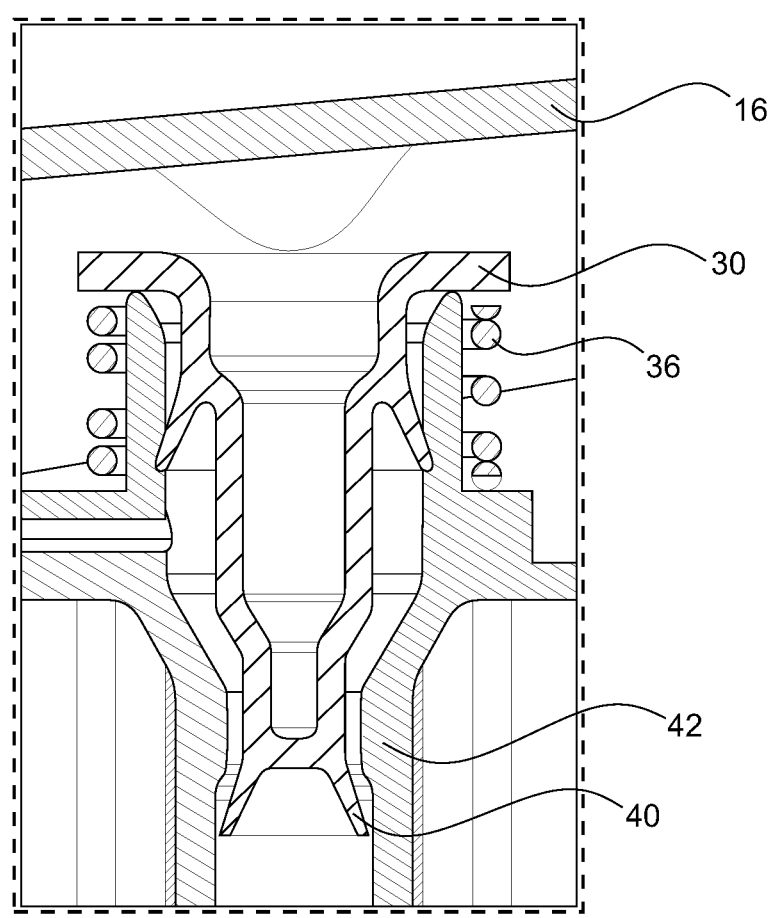
FIG. 6B is an enlarged view of the portion within the broken-line box labeled 6B in FIG. 3A.

Pulling on trigger 16 moves the trigger 16 from a first or home position, as shown in FIG. 2A and FIG. 6A, into a depressed or actuated position, as shown in FIG. 3A and FIG. 6B. This movement causes trigger 16 to press down on discharge valve 30, compressing spring 36, and moving discharge valve 30 into the position shown in FIG. 6B. In this position, enlarged portion 40 has been moved out of the reduced-diameter portion 42, thereby opening a fluid path in discharge passage 34 as shown. With the fluid path open, the force exerted by the vacuum pressure in vacuum cylinder 26 is sufficient to move head 12 upwards, thereby drawing piston 20 up through fluid cylinder 18 and discharging the contents of fluid cylinder 18 out through discharge passage 34 and discharge orifice 31.

In some embodiments of the invention, an orifice cup 29 may be positioned in discharge orifice 31 to control or define the spray characteristics of trigger sprayer 10. When the contents of fluid cylinder 18 have been fully discharged, the trigger sprayer 10 returns to its original configuration and is ready to be primed again for further dispensing.

Figure 4A:
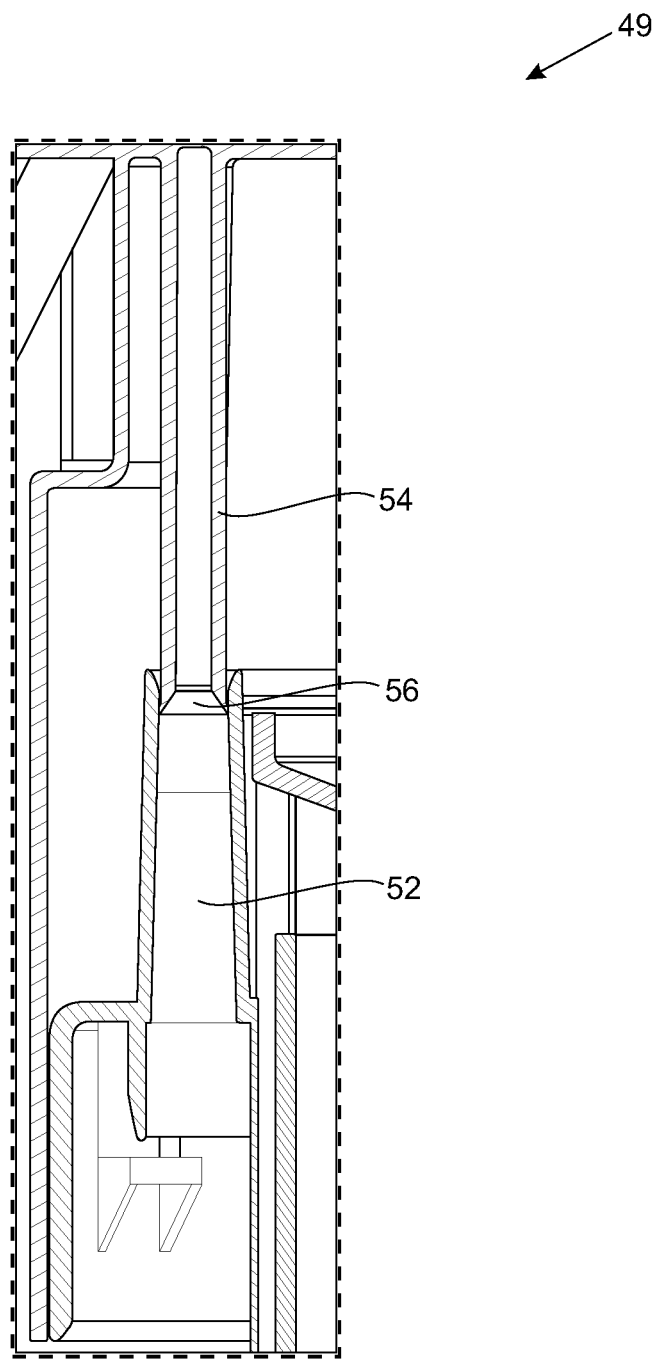
FIG. 4A is an enlarged view of the portion within the broken-line box labeled 4A in FIG. 2A.
Figure 4B:
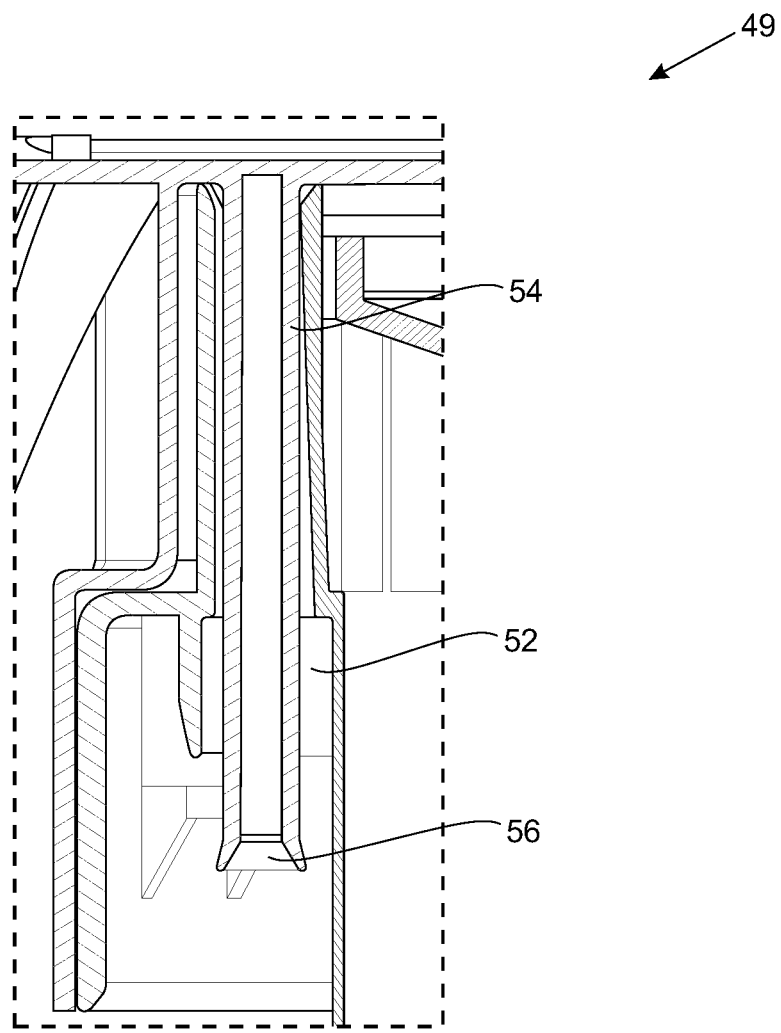
FIG. 4B is an enlarged view of the portion within the broken-line box labeled 4B in FIG. 3A.

FIGS. 4A and 4B illustrate enlarged views of various embodiments of a trigger sprayer's 10 venting system 49 in the trigger sprayer's 10 non-actuated and actuated positions, respectively. Venting system 49 includes an elongated, generally-vertical conduit 52 integrally formed as part of base 14. An elongated occlusion member 54, integrally formed as part of head 12, is reciprocally disposed within conduit 52. The interior diameter of conduit 52 may increase gradually moving downwardly from the conduit's top as illustrated. Occlusion member 54 may have an enlarged lower portion 56, seal ring, or other feature that may mate with or seal against an interior wall of the conduit 52. When the trigger sprayer 10 is in the shipping or non-actuated position as shown in FIG. 4A, enlarged lower portion 56 is snugly received within an upper, reduced-diameter portion of conduit 52, thereby sealing the venting system 49. When the trigger sprayer 10 is moved into its actuated position, enlarged lower portion 56 is moved out of the reduced-diameter portion of conduit 52, thereby opening an air path that allows venting of air into the container as fluid is dispensed.

A trigger sprayer 10 makes use of two separate vacuum systems, a first system to pull fluid into the fluid cylinder 18 and a second system to force discharge of the fluid cylinder's contents. These two vacuum systems are disposed "in-line" with one another, thereby saving space and simplifying the construction and operation of the trigger sprayer 10. The in-line configuration of the two vacuum systems advantageously allows a single motion (i.e., pushing down on head 12) to act on both systems simultaneously to fill the fluid cylinder 18 and prime the trigger sprayer 10 so that it is ready to discharge the fluid cylinder's contents upon the pulling of trigger 16. Another advantage of the trigger sprayer 10 as described herein is that the venting system 49 is open only when the trigger sprayer 10 is in the actuated/non-shipping position. Such a configuration reduces the risk of contamination and/or leaks of the container during shipment.

According to various embodiments of the invention, a trigger sprayer 10 may include may include a head 12, a base 14, and a trigger 16 as illustrated. The base 14 may be at least partially disposed within a portion of the head 12. Trigger 16 may be connected to, fixed to, or otherwise in communication with the head 12 as illustrated.

The head 12 of a trigger sprayer 10 according to various embodiments of the invention may include an outer shroud portion defining a cavity or interior space within the head 12. A portion of the base 14 may be disposed within a portion of the interior space of the head 12 as illustrated in FIGS. 2A and 2B. The head 12 may also include a piston rod 22 formed integrally therewith. The piston rod 22 may include a fluid discharge passage 34 defined therein, having a first opening adjacent a piston 20 connected to the piston rod 22 and a second opening adjacent a valve seat at an opposite end of the piston rod 22. A secondary discharge passage 72 may extend away from the valve seat to a discharge orifice 31 open to atmosphere. The discharge orifice 31, secondary discharge passage 72, and fluid discharge passage 34 may be in fluid communication with each other. For example, fluid or product flowing into the fluid discharge passage 34 of the piston rod 22 may flow past the valve seat into the secondary discharge passage 72 and out the discharge orifice 31.

According to some embodiments of the invention, a head 12 may also include an occlusion member 54 or vent valve formed integrally therewith. The occlusion member 54 may be configured to act as a vent closure or vent valve in conjunction with a portion of the base 14 as illustrated in FIGS. 4A and 4B.

A valve seat may also be formed integrally with the head 12 as illustrated in detail in FIG. 6A. The valve seat may include a reduced-diameter portion 42 in communication with the fluid discharge passage 34. An upper opening 74 opposite the reduced-diameter portion 42 may be configured to allow insertion of a discharge valve 30 into the valve seat. Various other configurations of a discharge valve 30 and valve seat may be incorporated into various embodiments of the invention. A fluid chamber 76 between the reduced-diameter portion 42 and the upper opening 74 may be in communication with the secondary discharge passage 72. In operation, fluid may pass from the discharge passage 34, past a portion of the discharge valve 30 into the fluid chamber 76 and out the secondary discharge passage 72.

A head 12 may also include one or more posts 78 configured to move a vacuum cylinder 26 upon actuation of the head 12. For example, as illustrated in FIGS. 2B and 3B, a head 12 according to various embodiments of the invention may include at least one post 78 which remains in contact with an upper surface of a vacuum cylinder 26. When head 12 is pushed downward, the one or more posts 78 push against the vacuum cylinder 26, causing movement of the vacuum cylinder 26 relative to the base 14. In addition, contact between the vacuum cylinder 26 and the one or more posts 78 allow the vacuum cylinder 26 to move head 12 upon actuation of the trigger 16. For instance, when the trigger sprayer 10 is charged or in a state ready for actuation and spraying as illustrated in FIGS. 3A and 3B, actuation of the trigger 16 opens the discharge valve 30 allowing fluid or product to escape the trigger sprayer 10 which in turn allows vacuum cylinder 26 to move, applying a force to the one or more posts 78, thereby moving head 12 upwards relative to the base 14.

Figure 5:
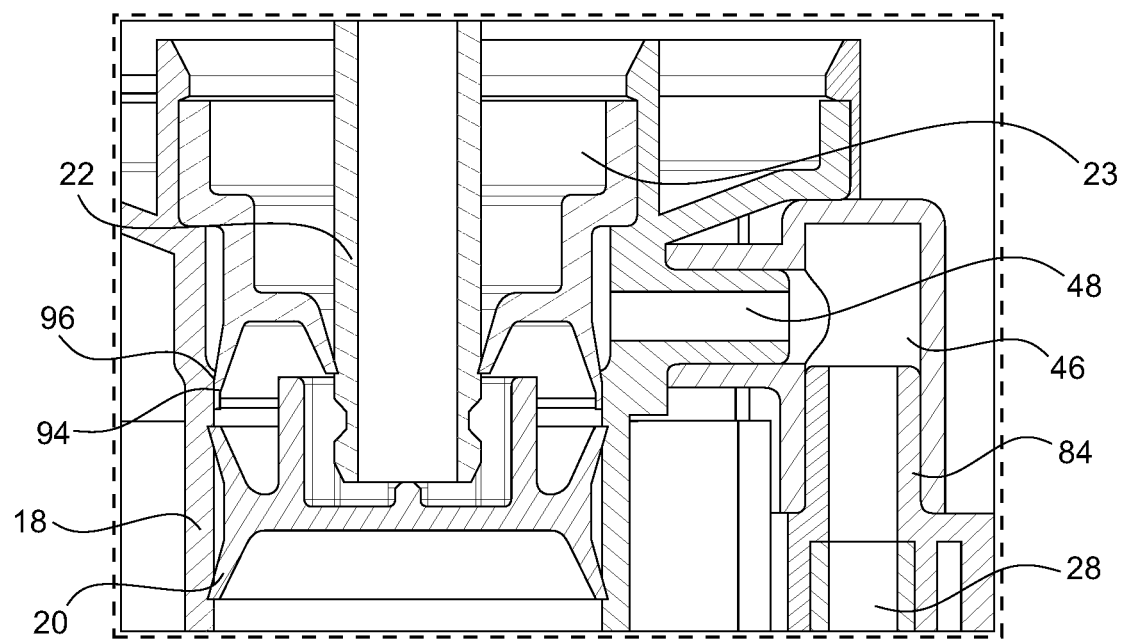
FIG. 5 is an enlarged view of the portion within the broken-line box labeled 5 in FIG. 2A.

A base 14 according to various embodiments of the invention may be configured to be attached to a container and to house certain internal working components of a trigger sprayer 10. In some embodiments, a base 14 may define a vacuum cylinder chamber 80 in which a vacuum cylinder 26 may move or travel. A dip tube holder 82 may also be formed in the base 14 and configured to hold a dip tube 28. A base 14 may also include an elbow attachment 84 to which an elbow 46 or other fluid pathway director may be attached to direct flow of a product from a container 900, through dip tube 28 and into a fluid cylinder 18 as illustrated in FIG. 5.

A base 14 may include connection points or systems to allow the base 14 and trigger sprayer 10 to be attached to a container 900. For example, base 14 may include a thread system for connecting the base 14 to a container 900 in a traditional screw-closure manner. In other embodiments, a base 14 may include bayonet-type connectors that may mate with or snap-fit onto corresponding connectors on a container 900 or container 900 neck. The base 14 may also include a plug seal as illustrated in various figures which may sit on or against an interior portion of a container 900 to seal the base 14 to the container 900 and to help prevent leakage of a product from the container 900.

In some embodiments of the invention, a base 14 may include a conduit 52 into which an occlusion member 54 of the head 12 may be positioned as illustrated in FIGS. 4A and 4B. The conduit 52 may be tapered or configured with a narrow top portion which engages the enlarged lower portion 56 of the occlusion member 54 in an air-tight seal at rest or in a non-primed position. A lower portion of the conduit 52 may widen so as not to engage the occlusion member 54 as it moves within the conduit 52. For example, as head 12 is moved downward or towards base 14 during priming of the trigger sprayer 10, the enlarged lower portion 56 may unseat from the air-tight fitment with the interior wall of the conduit 52. The break in the seal between the conduit 52 and the occlusion member 54 allows air from atmosphere to enter conduit 52 and container 900. In this manner, a vent for the trigger sprayer 10 is provided to allow venting of the container 900 during operation. As trigger sprayer 10 dispenses product, the head 12 moves upward, drawing occlusion member 54 back into an air-tight seal against the interior wall of the conduit 52.

A fluid cylinder 18 according to various embodiments of the invention may be supported by the base 14. The base 14 may include a fluid cylinder attachment to which the fluid cylinder 18 may attach. For example, a fluid cylinder 18 may snap into a base 14 as illustrated in FIG. 2A. Base 14 may include a snap bead about an upper end thereof configured to retain a fluid cylinder 18 in the base 14 as illustrated.

A fluid cylinder 18 may include a first end configured to retain a vacuum piston 24. A second end, opposite the first end, may include an opening. A fluid cylinder 18 may also include a fluid port 48. A fluid port 48 may be configured to allow fluid or product to flow into an interior of the fluid cylinder 18.

According to various embodiments of the invention, a piston 20 may be inserted into the opening in fluid cylinder 18. The piston 20 may be attached to the piston rod 22 of the head 12 as illustrated in FIGS. 2A and 2B. An interior portion of the first end, interior walls of the fluid cylinder 18, and a lower surface of piston 20 may define a piston chamber 92 within the fluid cylinder 18 through which the piston 20 may move along with movement of the head 12.

A static seal 23 may be seated within the opening of the fluid cylinder 18 adjacent the piston 20. The static seal 23 may include a valve seal 94 which contacts an interior surface of the fluid cylinder 18 at rest as illustrated in FIG. 5. In some embodiments of the invention, the fluid cylinder 18 may include a seal lip 96 adjacent the contact point of the static seal 23 with the fluid cylinder 18 as illustrated. In other embodiments, the valve seal 94 may seal against an interior surface alone. As illustrated, a static seal 23 may be seated adjacent the fluid port 48. The static seal 23 may prevent fluid or product from flowing from a container 900 into an interior of the fluid cylinder 18. For instance, as illustrated in FIG. 5, when at rest, the valve seal 94 of the static seal 23 seats against an interior wall of the fluid cylinder 18, preventing fluid or product coming through the fluid port 48 into the fluid cylinder 18. However, if the valve seal 94 is unseated, fluid or product may flow from the fluid port 48 into an interior portion of the fluid cylinder 18.

For example, filling of a portion of the fluid cylinder 18 with product is illustrated in FIGS. 2A, 2B, 3A, and 3B. At rest, static seal 23 seals off an interior portion of the fluid cylinder 18 from fluid port 48. As head 12 is pushed downward, piston rod 22 is moved which in turn moves piston 20 within the fluid cylinder 18. As piston 20 moves, a vacuum or pressure differential is formed within the fluid cylinder 18 between an upper surface of the piston 20 and the valve seal 94 portion of the static seal 23. The pressure differential is sufficient to lift or unseal valve seal 94 from contact with the interior wall of fluid cylinder 18. The pressure differential is also sufficient to draw fluid or product from a container 900 or other source through fluid port 48 and into an interior space of the fluid cylinder 18. Once head 12 is partially or completely depressed, the fluid cylinder chamber 98 illustrated in FIGS. 3A and 3B is filled with product or fluid.

Simultaneously, as head 12 is moved or depressed, head 12 moves the vacuum cylinder 26 downward relative to the vacuum piston 24. Movement of the vacuum cylinder 26 relative to the vacuum piston 24 creates a vacuum chamber 100 defined by the interior walls of the vacuum cylinder 26 and a lower portion of the vacuum piston 24 as illustrated in FIGS. 3A and 3B.

Upon actuation of trigger 16, discharge valve 30 is unseated, creating a fluid flow path through the discharge passage 34 and secondary discharge passage 72 and out the discharge orifice 31. The pressure differential between the vacuum chamber 100 and atmosphere draws the vacuum cylinder 26 upwards which in turn applies force to the head 12 through one or more posts 78 which in turn pulls piston 20 up through the fluid cylinder 18 allowing fluid in the fluid cylinder chamber 98 to flow past openings in the piston 20 and into the discharge passage 34.

As illustrated in FIG. 3A, piston 20 may include one or more passageways 102 in an upper surface thereof. The one or more passageways 102 may be in fluid communication with the discharge passage 34 such that fluid or product may flow from the fluid cylinder chamber 98 through the one or more passageways 102 and into the discharge passage 34.

In various embodiments of the invention, a vacuum piston 24 is attached to the first end of the fluid cylinder 18 as illustrated. The vacuum piston 24 may include an integrated valve 50 in communication with an opening in the first end of the fluid cylinder 18 as illustrated in FIG. 2A. The integrated valve 50 may be a one-way valve configured to allow air to pass through the integrated valve 50 during assembly of the trigger sprayer 10. For example, when fluid cylinder 18 with a vacuum piston 24 is inserted into the vacuum cylinder 26 during assembly, air trapped within the vacuum cylinder 26 must escape. Pressure build-up within the vacuum cylinder 26 may crack the integrated valve 50, allowing air to escape from within the vacuum cylinder 26 into an interior space of the fluid cylinder 18. Thus, the vacuum piston 24 may be inserted completely within the vacuum cylinder 26.

While various embodiments of the invention have been described with respect to a trigger 16 actuated spray device, it is understood that other actuation methods could be used. For example, trigger 16 may be replaced with a button or other actuation device such that as user depresses a button, the discharge valve 30 is opened to allow spray of a product from the trigger sprayer 10, or other sprayer device.

While various embodiments of the invention are described herein, it is understood that the particular embodiments defined by the appended claims are not to be limited by particular details set forth in the description, as many apparent variations thereof are contemplated. Rather, embodiments of the invention are limited only by the appended claims, which include within their scope all equivalent devices or methods which operate according to the principles of the embodiments of the invention described.

What is claimed is:

1. A trigger sprayer, comprising:
   a housing comprising a head and a base, the head and base being configured to move relative to one another between a non-actuated position and an actuated position, wherein the base is at least partially disposed within an interior of the head in the actuated position;
   a first vacuum system comprising a fluid cylinder, the first vacuum system being configured to draw fluid into the fluid cylinder when the trigger sprayer is moved from the non-actuated position to the actuated position; and
   a second vacuum system comprising a vacuum cylinder, the second vacuum system being configured to form a vacuum within the vacuum cylinder when the trigger sprayer is moved from the non-actuated position to the actuated position, wherein the vacuum is configured to exert a force on the head sufficient to cause the fluid to be discharged from the fluid cylinder when a fluid path between the fluid cylinder and a discharge orifice of the trigger sprayer is opened,
   wherein the second vacuum system further comprises a vacuum piston mounted at a lower end of the fluid cylinder.

2. The trigger sprayer of claim 1, further comprising a spring-biased discharge valve configured to be moved between a closed position in which the fluid path is closed and an open position in which the fluid path is open, the discharge valve being configured to move from the closed position into the open position in response to activation of a trigger.

3. The trigger sprayer of claim 1, wherein the first vacuum system further comprises a piston reciprocally disposed within the fluid cylinder.

4. The trigger sprayer of claim 3, wherein the piston is fixedly mounted at a lower end of a hollow piston rod, an interior of the hollow piston rod defining at least a part of a discharge passage between the fluid cylinder and the discharge orifice.

5. The trigger sprayer of claim 4, wherein the hollow piston rod is fixedly mounted within the head.

6. The trigger sprayer of claim 1, wherein the first vacuum system further comprises a static seal disposed within an upper end of the fluid cylinder, the static seal being configured to deform so as to allow the fluid to enter the fluid cylinder when the trigger sprayer moves from the non-actuated to the actuated position.

7. The trigger sprayer of claim 1, wherein the vacuum piston comprises an integrated valve configured to vent air out of the vacuum cylinder during assembly of the trigger sprayer.

8. The trigger sprayer of claim 1, further comprising a venting system, wherein the venting system is configured to be sealed when the trigger sprayer is in the non-actuated position and open when the trigger sprayer is in the actuated position.

9. A trigger sprayer, comprising:
   a head, comprising:
     an outer shroud;
     a piston rod;
     a fluid discharge passage in the piston rod;
     a secondary discharge passage in fluidic communication with the discharge passage; and
     a valve seat between the fluid discharge passage and the secondary discharge passage;
   a discharge valve seated in the valve seat;
   a base, comprising:
     a container connection; and
     a vacuum cylinder chamber;
   a fluid cylinder connected to the base, comprising:
     a lower end;
     an upper end comprising an opening; and
     a fluid port;
   a vacuum cylinder positioned at least partially in the vacuum cylinder chamber and surrounding at least a portion of the fluid cylinder;
   a vacuum piston attached to the lower end of the fluid cylinder and in contact with an interior wall of the vacuum cylinder;
   a piston mounted on the piston rod and in contact with an interior wall of the fluid cylinder; and
   a static seal mounted on the fluid cylinder, the static seal comprising a valve seal moveably seated against the interior wall of the fluid cylinder between the piston and the fluid port.

10. The trigger sprayer of claim 9, wherein the head further comprises at least one post wherein the at least one post is in contact with the vacuum cylinder.

11. The trigger sprayer of claim 9, wherein the head further comprises an occlusion member.

12. The trigger sprayer of claim 11, wherein the base further comprises a conduit and wherein the occlusion member is seated in the conduit.

13. The trigger sprayer of claim 12, wherein the occlusion member is sealed against an inner wall of the conduit.

14. The trigger sprayer of claim 12, wherein the movement of the head unseats the occlusion member relative to the conduit.

15. The trigger sprayer of claim 9, wherein the base further comprises a dip tube holder.

16. The trigger sprayer of claim 9, further comprising an elbow connected to an elbow attachment on the base and the fluid port.

17. The trigger sprayer of claim 9, wherein the base further comprises a fluid cylinder attachment.

* * * * *